United States Patent
De Mattia

(10) Patent No.: US 9,417,167 B2
(45) Date of Patent: Aug. 16, 2016

(54) METHOD FOR TESTING A BATCH OF MATERIAL USED FOR OBTAINING LAYERS OF FIBRES INTENDED FOR MANUFACTURING A COMPOSITE MATERIAL COMPONENT

(71) Applicant: Airbus Operations S.A.S., Toulouse (FR)

(72) Inventor: Denis De Mattia, Basse Goulaine (FR)

(73) Assignee: Airbus Operations S.A.S. (FR)

(*) Notice: Subject to any disclaimer, the term of this patent is extended or adjusted under 35 U.S.C. 154(b) by 8 days.

(21) Appl. No.: 14/494,670

(22) Filed: Sep. 24, 2014

(65) Prior Publication Data

US 2015/0090047 A1   Apr. 2, 2015

(30) Foreign Application Priority Data

Sep. 27, 2013   (FR) ..................................... 13 59349

(51) Int. Cl.
| | |
|---|---|
| *G01N 3/08* | (2006.01) |
| *G01N 3/18* | (2006.01) |
| *B29C 70/54* | (2006.01) |
| *G01B 21/32* | (2006.01) |
| *B29C 70/20* | (2006.01) |

(52) U.S. Cl.
CPC  *G01N 3/18* (2013.01); *B29C 70/20* (2013.01); *B29C 70/54* (2013.01); *G01B 21/32* (2013.01); *G01N 2203/0017* (2013.01)

(58) Field of Classification Search
CPC ................ G01N 2203/0224; G01N 2203/028; G01N 3/08; G01N 3/18; G01B 21/32
USPC ...................................... 73/826, 828, 862.392
See application file for complete search history.

(56) References Cited

U.S. PATENT DOCUMENTS

| | | | | |
|---|---|---|---|---|
| 5,188,456 A | * | 2/1993 | Burke | G01N 3/08 374/50 |
| 7,811,495 B2 | | 10/2010 | Dagher et al. | |
| 2002/0136262 A1 | * | 9/2002 | Feger | G01N 25/16 374/55 |
| 2006/0288794 A1 | * | 12/2006 | Hardwicke | G01L 1/2287 73/763 |

FOREIGN PATENT DOCUMENTS

| | | |
|---|---|---|
| GB | 2 169 480 A | 7/1986 |
| JP | 2000 071409 A | 3/2000 |

OTHER PUBLICATIONS

Lee K-G et al, "The development of structure and mechanical properties in poly(ethylene terephthalate) fibres during heat treatment under stress," Polymer, Elsevier Science Publishers B.V, GB, vol. 34, No. 21, Nov. 1, 1993, pp. 4455-4470, XP024116079.
French Search Report (FR 13 59349) (Jun. 2, 2014).

* cited by examiner

*Primary Examiner* — Max Noori
(74) *Attorney, Agent, or Firm* — Lerner, David, Littenberg, Krumholz & Mentlik, LLP

(57) ABSTRACT

A method for testing a batch of material used to obtain layers of fibers includes taking a specimen from the batch of material, exerting a tensile force on the specimen, heating the specimen so as to relax the fibers if the specimen contains stresses, after a predetermined period of time, no longer heating and no longer exerting the tensile force on the specimen, measuring a residual extension of the specimen which corresponds to a variation in length of at least a part of the specimen in the direction of the tensile force, before and after the tensile force, and considering the batch of material not to be compliant if the residual extension exceeds a given threshold.

14 Claims, 1 Drawing Sheet

METHOD FOR TESTING A BATCH OF MATERIAL USED FOR OBTAINING LAYERS OF FIBRES INTENDED FOR MANUFACTURING A COMPOSITE MATERIAL COMPONENT

FIELD OF THE INVENTION

The present invention relates to a method for testing a batch of material used to obtain layers of fibres intended for manufacturing a composite material component, and also to a method for manufacturing a composite material component that comprises said test method.

BACKGROUND OF THE INVENTION

In the aerospace domain, composite materials are being used more and more to reduce the mass of an aircraft. A composite material component comprises fibres, for example made of carbon, that are embedded in a matrix of resin, for example thermosetting resin.

In one mode of operation, firstly, a preform of fibres, preferably pre-impregnated fibres, is produced and subsequently polymerized in particular in an autoclave so as to obtain the final component.

In order to obtain the preform of fibres, layers of fibres are stacked successively one on top of another, the fibres being oriented in at least one predetermined direction for each layer depending on the mechanical characteristics that are desired.

In order to increase productivity, automatic machines such as those referred to as ATL (Automated Tape Laying) machines are used to produce the stack of layers of fibres.

According to one embodiment, the layers of fibres are cut out of a strip of fibres stored in the form of a reel, the strip of fibres being pressed against a support in the form of a film of paper or plastics material that has the role of a separator when the strip is wound on a reel.

The absence of undulations in the fibres is an important criterion for the quality of the final component.

The undulations in the fibres may originate from the layers of fibres or be generated during the stacking of the layers or during polymerization.

Thus, prior to being placed in position, the layers of fibres can have stresses which tend to generate the undulations of fibres in the layers of fibres.

For example, during the production of the strip of fibres, when the support is in the stretched state at the time when the fibres are placed thereon, the releasing of the extension of the support will bring about compression of the fibres, which will undulate and remain in this state in the preform of fibres.

According to another aspect, with the strip of fibres wound on a reel, there is a difference in tension between the fibres close to the internal surface and those close to the external surface, resulting in there being compressed fibres in the region of the internal surface of the strip of fibres wound on a reel. This compressed state of the fibres in the region of the internal surface is even greater, the thicker the strip and the smaller the winding radius. In the case of a strip of fibres wound on a reel and close to its expiration date, the resin that impregnates the fibres is "drier" such that the fibres close to the internal surface tend to retain their undulations during the stacking of the layers of fibres.

There are no non-destructive tests that ensure the absence of undulations in fibres. The only test that is possible consists in cutting up a finished component into localized sections in order to observe the layers of fibres under a microscope.

However, this test phase is only possible at the end of the method for manufacturing the components. Consequently, if the layer of fibres has a defect prior to stacking, this is only detected at the end of the method and the steps of depositing layers and polymerization are carried out in vain.

SUMMARY OF THE INVENTION

Aspects of the present invention may remedy the drawbacks of the prior art.

An aspect of the invention is a method for testing a batch of material used to obtain layers of fibres so as to determine, before it is used to produce a preform of fibres with the aim of obtaining a composite material component, whether the batch of material is compliant and there is no risk of it bringing about undulations in the composite material component that is obtained.

According to an aspect of the invention, the test method is characterized in that it comprises the following steps that consist in:

taking a specimen comprising fibres from the batch of material, exerting a tensile force on the specimen, heating the specimen so as to relax the fibres if the specimen contains stresses, after a predetermined period of time, no longer heating and no longer exerting the tensile force on the specimen, measuring a residual extension of the specimen which corresponds to a variation in length of at least a part of the specimen in the direction of the tensile force, before and after the tensile force, considering the batch of material not to be compliant if the residual extension exceeds a given threshold.

According to one feature, the tensile force is greater than or equal to 4 daN/mm$^2$ of cross-sectional area of the specimen.

Preferably, the specimen is tautened and kept taut before and after the tensile force during the measurement of the residual extension. Advantageously, a force of around 0.16 daN/mm$^2$ of cross-sectional area of the specimen is applied to tauten the specimen.

According to one mode of operation, the specimen is heated to a temperature of around 100° C.

According to another feature, the specimen is in the form of a strip having a length of around 10 m, the tensile force being exerted along the length of the specimen.

Preferably, the fibres of the specimen are oriented in the direction of the tensile force.

According to one mode of operation, the specimen comprises a fixed first end which is connected to a fixed point of a reference element, and a movable second end at which a force is exerted. In this case, preferably a first mark is provided on the specimen in the vicinity of the second end and a second mark is provided on the reference element, the first mark and the second mark being disposed in a direction intersecting the direction of the tensile force, the residual extension corresponding to the variation in length before and after the tensile force between the first mark and the second mark.

According to another feature, for a specimen having a length of 10 m and a width of around 6 mm, the threshold is around 0.8 mm for a batch of material having a density of 270 g/m$^2$ of pre-impregnated fibres.

According to another feature, for a specimen having a length of 10 m and a width of around 6 mm, the threshold is around 1 mm for a batch of material having a density of 198 g/m$^2$ of pre-impregnated fibres.

According to another feature, for a specimen having a length of 10 m and a width of around 6 mm, the threshold is around 1.2 mm for a batch of material having a density of 135 g/m² of pre-impregnated fibres.

The invention also relates to a method for manufacturing a composite material component, comprising a method for testing a batch of material used to obtain layers of fibres, prior to the use of said layers of fibres.

BRIEF DESCRIPTION OF THE DRAWINGS

Further features and advantages will become apparent from the following description of the invention, this description being given purely by way of example, with reference to the appended drawings

DETAILED DESCRIPTION

Figure 1A:
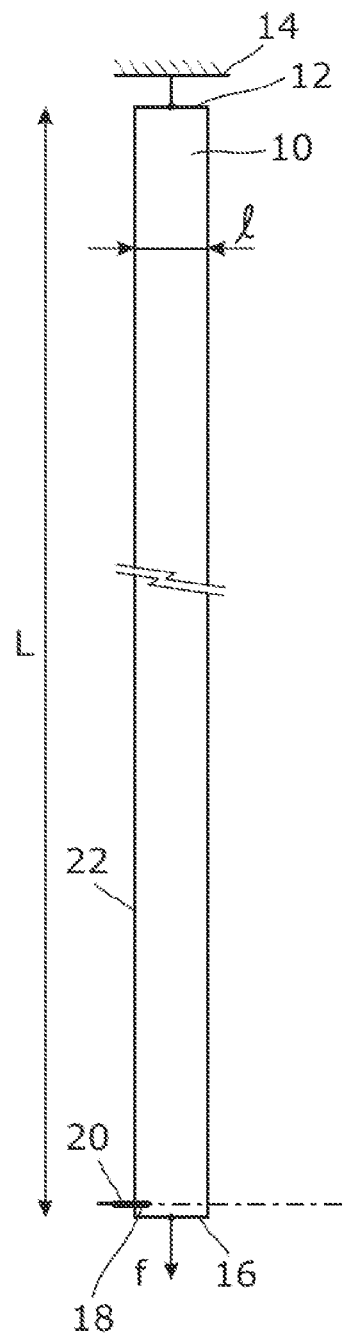
FIGS. 1A-1C illustrate elevational view of a specimen during different steps of a method according to an aspect of the invention.

According to one mode of operation, a composite material component is obtained by polymerizing a preform of fibres which comprises a stack of layers of fibres. Preferably, the fibres are pre-impregnated with a resin. By way of example, the fibres are made of carbon and the resin is a thermosetting resin.

The layers of fibres are cut out of a strip of fibres, namely an element having a long length compared with its width.

As an idea of an order of magnitude, the strip of fibres has a thickness less than 1 mm, a width of around 150 to 300 mm and a length greater than or equal to 10 m.

The strip of fibres comprises fibres that are oriented in at least one predetermined direction depending on the mechanical properties that are desired for the component.

The strip of fibres is generally stored in the form of a reel. Advantageously, a substrate in the form of a fine film of paper and/or plastics material is pressed against at least one of the faces of the strip in order to act as a separator when the strip is wound on a reel.

The nature of the fibres and of the resin, the dimensions of the layers, the mode of operation of stacking and the mode of operation of polymerization are not described in more detail since they are known to a person skilled in the art.

In any case, the layers of fibres come from a batch of material which is in the form of a reel in one storage mode. Other arrangements may be envisaged for the batch of material, for example folding in the manner of an accordion.

Before it is used to form layers of fibres which will then be stacked one on another in order to obtain a preform, the batch of material is tested so as to verify whether it comprises stresses that are liable to generate undulations in fibres in the preform. This solution makes it possible to avoid the use of a defective batch for manufacturing composite material components.

According to one mode of operation, the method for testing the batch of material used to obtain layers of fibres comprises the steps that consist in:
  taking a specimen 10 from the batch of material,
  exerting a tensile force F on the specimen 10,
  heating the specimen 10 so as to relax the fibres if the specimen contains stresses, for example undulations or micro-undulations of fibres,
  after a predetermined period of time, no longer heating and no longer exerting a tensile force F on the specimen 10,
  measuring a residual extension of the specimen 10,
  considering the batch of material not to be compliant if the residual extension exceeds a given threshold.

The residual extension corresponds to a variation in length of at least a part of the specimen 10 in the direction of the tensile force F, before and after the tensile force F has been exerted. It is denoted d in FIG. 1C.

The tensile force F should be significant and greater than or equal to 4 daN/mm² of cross-sectional area of the specimen, so as to allow the fibres to extend, eliminating the undulations which they may have when they are held by the resin at 20° C. Thus, the tensile force F depends on the cross-sectional area of the specimen. For each cross-sectional area, the surface of the section of the fibre is extended in a plane perpendicular to the length of the fibre.

Advantageously, the specimen 10 is cut out along the length of the strip of fibres when the batch of material is in the form of a reel with a great width (150 or 300 mm).

Preferably, the specimen 10 has a length L of around 10 m in order that the residual extension is significant and thus easy to measure.

According to one embodiment, the specimen 10 has a length of around 10 m and a width l of around 6 to 10 mm.

According to another feature of the invention, the tensile force F is exerted in a direction parallel to the length of the specimen, the length corresponding to the largest dimension of the specimen.

Advantageously, the specimen 10 is cut out of the batch of material such that the fibres of the specimen are oriented in the direction of the tensile force F.

According to one embodiment, the specimen 10 comprises a fixed first end 12, connected to a fixed point of a reference element 14 such as a table, and a movable second end 16 at which a force is exerted. The first end 12 is connected to a fixed point so as to ensure the absence of slip between the first end 12 and the reference element 14.

According to one mode of operation, before the tensile force F is exerted, a first mark 18 is provided on the specimen 10 in the vicinity of the second end 16 and a second mark 20 is provided on a fixed reference element 14, for example the table, the first mark 18 and the second mark 20 being disposed in a direction intersecting the direction of the tensile force F and preferably perpendicular to the direction of the tensile force F. The first mark 18 and the second mark 20 are advantageously lines. According to one embodiment, the first mark 18 extends from one edge 22 of the specimen and the second mark 20 is disposed in line with the first mark 18.

According to this mode of operation, in order to determine the residual extension, the distance between the first mark 18 and the second mark 20 should be measured when the tensile force F is no longer being exerted.

According to one feature of the invention, during the tensile force F, the specimen is brought to a temperature of around 100° C. According to one embodiment, use is made of a hot-air gun which is moved slowly, for example at around 100 mm/s, in front of the specimen, along its length, carrying out a number of back-and-forth movements, around ten, such that the fibres which potentially have undulations have time to relax under the effect of the tensile force.

Preferably, the specimen is tautened and kept taut before and after the tensile force F, during the measurement of the residual extension. To this end, a force f is exerted at at least one end of the specimen 10, in particular at the second end 16.

The tensile force F is much greater than the force f. "Much greater" means that the tensile force F is at least 20 times greater than the force f.

As an idea of an order of magnitude, the force f is around 0.16 daN/mm² of cross-sectional area of the specimen. The tensile force F is around 8 daN/mm² of cross-sectional area of the specimen.

The provision of the marks 18 and 20 is carried out with the specimen 10 taut and the residual extension is carried out with the specimen kept taut.

The threshold value beyond which the batch of material is no longer compliant and risks bringing about defects in the final component varies in particular depending on the nature of the fibres and the resin, on the arrangement and density of the fibres, and on the length and the width of the specimen.

For a specimen 10 having a length of 10 m and a width of around 6 mm, the threshold is around 0.8 mm for a batch of material having a density of 270 g/m² of pre-impregnated fibres, around 1 mm for a batch of material having a density of 198 g/m² of pre-impregnated fibres and around 1.2 mm for a batch of material having a density of 135 g/m² of pre-impregnated fibres.

Figure 1B:
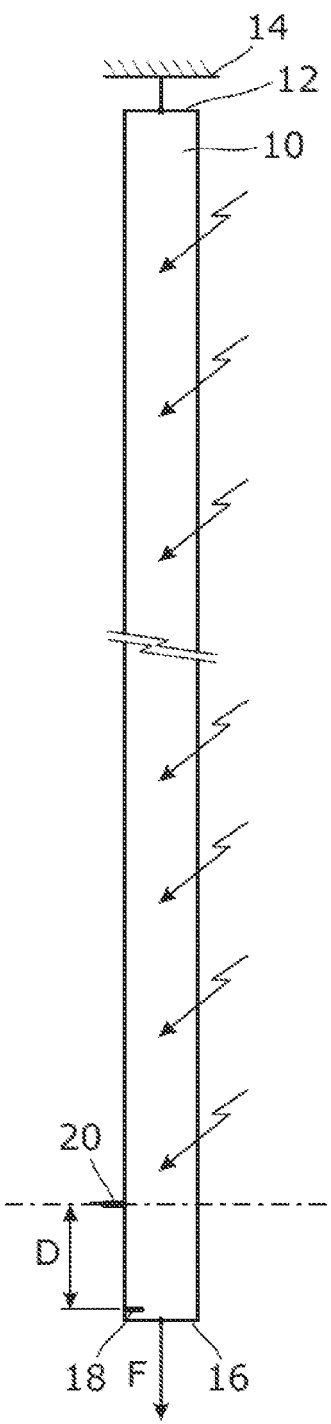
Figure 1C:
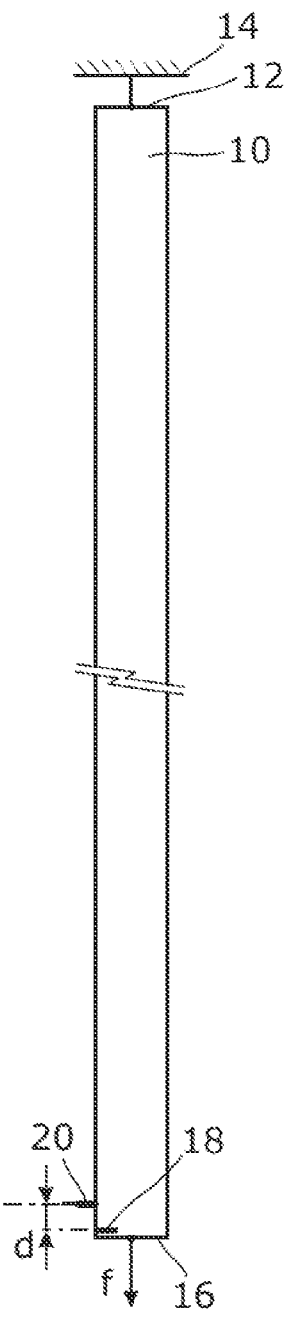

One mode of operation is shown in FIGS. 1A to 1C.

Firstly, as illustrated in FIG. 1A, the first end 12 of the specimen 10 is attached to the reference element 14 and the specimen 10 is tautened by exerting a force f at the second end 16. The marks 18 and 20 are provided on the specimen 10 and the reference element 14, respectively.

Next, as illustrated in FIG. 1B, a tensile force F is exerted and the specimen 10 is heated.

After a period of around 15 minutes, heating of the specimen 10 is stopped and the tensile force F is released down to the force f. On returning to the force f, the distance between the two marks 18 and 20 is measured, as illustrated in FIG. 1C. If this distance, which corresponds to the residual extension d, exceeds a given threshold, the batch of material is declared non-compliant and is not used to produce composite material components.

The invention claimed is:

1. A method for testing a batch of material used to obtain layers of fibres, the method comprising:
   taking a specimen comprising fibres from the batch of material;
   exerting a tensile force on the specimen for a predetermined period of time;
   heating the specimen for the predetermined period of time by moving a heat source along a length of the specimen; and
   measuring a residual extension of the specimen, the residual extension corresponding to a variation in length of at least a part of the specimen in the direction of the tensile force, before and after the exertion of the tensile force.

2. The method according to claim 1, further comprising determining the batch of material to be non-compliant if the residual extension exceeds a given threshold.

3. The method according to claim 1, wherein the tensile force is greater than or equal to 4 daN/mm² of cross-sectional area of the specimen.

4. The method according to claim 1, wherein the specimen is tautened and kept taut before and after the tensile force during the measurement of the residual extension.

5. The method according to claim 4, wherein a force of around 0.16 daN/mm² of cross-sectional area of the specimen is applied to tauten the specimen.

6. The method according to claim 1, wherein the specimen is heated to a temperature of around 100° C.

7. The method according to claim 1, wherein the specimen is in the form of a strip having a length of around 10 m, the tensile force being exerted along the length of the specimen.

8. The method according to claim 1, wherein the fibres of the specimen are oriented in the direction of the tensile force.

9. The method according to claim 1, wherein the specimen comprises a fixed first end connected to a fixed point of a reference element, and a movable second end at which a force is exerted.

10. The method according to claim 9, further comprising:
    providing a first mark on the specimen in the vicinity of the second end; and
    providing a second mark on the reference element, the first mark and the second mark being disposed in a direction intersecting the direction of the tensile force, the residual extension corresponding to the variation in length before and after the exertion of the tensile force between the first mark and the second mark.

11. The method according to claim 1, wherein, for a specimen having a length of 10 m and a width of around 6 mm, the threshold is around 0.8 mm for a batch of material having a density of 270 g/m² of pre-impregnated fibres.

12. The method according to claim 1, wherein, for a specimen having a length of 10 m and a width of around 6 mm, the threshold is around 1 mm for a batch of material having a density of 198 g/m² of pre-impregnated fibres.

13. The method according to claim 1, wherein, for a specimen having a length of 10 m and a width of around 6 mm, the threshold is around 1.2 mm for a batch of material having a density of 135 g/m² of pre-impregnated fibres.

14. A method for manufacturing a composite material component, comprising testing a batch of material of layers of fibres prior to use of said layers of fibres, the method for testing comprising:
    taking a specimen comprising fibres from the batch of material;
    exerting a tensile force on the specimen for a predetermined period of time;
    heating the specimen for the predetermined period of time by moving a heat source along a length of the specimen so as to relax the fibres if the specimen contains stresses; and
    measuring a residual extension of the specimen, the residual extension corresponding to a variation in length of at least a part of the specimen in the direction of the tensile force, before and after the exertion of the tensile force.

* * * * *